United States Patent [19]

Winner

[11] Patent Number: Plant 7,609

[45] Date of Patent: Jul. 30, 1991

[54] VARIETY OF GERANIUM NAMED SUNSET

[75] Inventor: Blair L. Winner, Lompoc, Calif.

[73] Assignee: Denholm Seeds, Lompoc, Calif.

[21] Appl. No.: 519,091

[22] Filed: May 4, 1990

[51] Int. Cl.[5] ..... A01H 5/00

[52] U.S. Cl. ..... Plt./68

[58] Field of Search ..... Plt./68

*Primary Examiner*—James R. Feyrer

*Attorney, Agent, or Firm*—Webb, Burden, Ziesenheim & Webb

[57] ABSTRACT

A new cultivar is characterized by its compact well branched plant form with the bloom placed uniformly above the medium green foliage. New variety has a pleasing cherry scarlet color and holds up well under outdoor conditions.

1 Drawing Sheet

BACKGROUND OF THE INVENTION

The present invention comprises a new and distinct cultivar of the *Pelargonium*×*hortorum* known by the varietal name Sunset (Oglevee No. 873; Denholm Seeds No. 42090-1). The new variety was discovered in a selective breeding program by Mr. Blair Winner in August of 1982 in Lompac, Calif. The new variety is a selection from the cross of Glacier Crimson (formerly known as Bruni), U.S. Plant Pat. No. 5,057 and the unpatented variety Sincerity.

The new variety was first asexually reproduced by cuttings at Denholm Seeds in Lompoc, Calif. following its discovery. The new variety has been repeatedly asexually reproduced by cuttings at Oglevee Ltd. in Connellsville, Pa. over a several year period. It has been trial and field tested at Connellsville and it has been found to retain its distinctive characteristics through successive propagations.

The new variety forms a taller plant than Glacier Crimson and more along the lines of Sincerity. The flower color is a more cherry scarlet while Sincerity is a light scarlet.

The new cultivar when grown in a glass greenhouse in Connellsville, Pa. using natural light and 60° F. (night), 68° F. (day), and 71° F. (vent) has a response time of 6 weeks from a rooted cutting to flowering in a 10 centimeter pot. This response time was determined on plants grown in a soilless media employing constant fertilizer of 250 to 300 parts per million of nitrogen and potassium and in full light. The rooted cuttings were potted Aug. 1, 1988 and flowered Sept. 15, 1988.

DESCRIPTION OF THE DRAWING

FIG. 1 of the accompanying photographic drawing illustrates the new cultivar, the color being as nearly true as possible with color illustrations of this type.

DESCRIPTION OF THE NEW PLANT

The following detailed description sets forth the characteristics of the new cultivar. The data which define these characteristics were collected by asexual reproductions carried out by Oglevee Ltd. in Connellsville, Pa. The plant history was taken on six week plants blossomed under natural light in a greenhouse and color readings were taken indoors under 200-220 foot candles of cool, white fluorescent light. Color references are primarily to The R.H.S. Colour chart of The Royal Horticultural Society of London.

THE PLANT

Classification:
- *Botanical.*—*Pelargonium*×*hortorum.*
- *Commercial.*—Zonal Florists Geranium.

Form: Semi-dwarf; compact growth; free basal branching; free and early flowering; upright habit.
Height: 18-22 cm above media surface.
Growth: Short internodes; free branching from base.
Strength: Stands upright without artificial support.
Foliage: Faint zone present; stalked leaf attachment.
Leaves:
- *Size.*—6-9 cm across (fully expanded leaf).
- *Shape.*—Reniform; cordate base.
- *Margin.*—Crenate.
- *Texture.*—Pubsecent; dull (not reflective).
- *Color.*—Top: Outer Margin: Green Group 137B. Top: Inner Margin: Green Group 137D. Bottom: Yellow-Green Group 146B.
- *Ribs and veins.*—*Palmate venation; Yellow-Green* 146D.

Petioles: 5-8 cm in length; Yellow-Green Group 146B.
Stem:
- *Color.*—Yellow-green Group 146C.
- *Internodes.*—1-2 cm in length.

THE BUD

Shape: Upright; hemispherical cluster.
Size: 1.5-2.5 cm across.

INFLORESCENCE

Blooming habit: Continuous; upright; semi-double; hemispherical slow to shatter.
Size: 8-10 cm when fully open.
Borne: Umbel; 5-8 cm above foliage; florets on pedical; pedicel on peduncle.
Florets:
- *Form.*—Flat to slightly cupped; obovate.
- *Color.*—Top: Red Group 43A. Bottom: Red Group 43C.
- *Petals.*—5-7 in number; separate; not united; margin entire; smooth; flat to slightly cupped.
- *Size.*—2-3 cm across.
- *Texture and appearance.*—Smooth.

Petaloids:
- *Quantity.*—3-5.
- *Shape.*—Narrow, elongated, twisted.

*Color.*—Top: Red Group 43A. Bottom: Red Group 43C.

Pedicel:

*Length.*—2.5–3 cm in length.

*Color.*—Bottom: Yellow-Green Group 146C. Top: Red-Purple Group 59B.

Peduncle:

*Length.*—8–11 cm in length.

Disease resistance: Not known.

REPRODUCTIVE ORGANS

Stamens:

*Anthers.*—1–2 mm in length.

*Filaments.*—0.5–1 cm in lengths; white at base to pink at tip; irregular in shape.

*Pollen.*—Golden brown to yellow.

Pistils:

*Number.*—1 with 5 part stigma.

*Length.*—8–9 mm in length.

*Stigma.*—1; 5 parted at maturity; Red-Purple in color.

*Style.*—3–4 mm in length.

Ovaries: Superior; pale green; very pubescent; 4–5 mm in length; 2–3 mm across.

Fruit: None observed.

This new and distinct Geranium variety is similar in color to Irene, which is currently on the market, but Sunset does not show petal burn. The plant form is compact, well branched and the bloom is placed uniformly above the medium green foliage. This new cultivar has a much neater plant habit, flower form and color than Irene and it holds up very well outdoors.

I claim:

1. A new and distinct variety of Geranium plant substantially as shown and described.

* * * * *

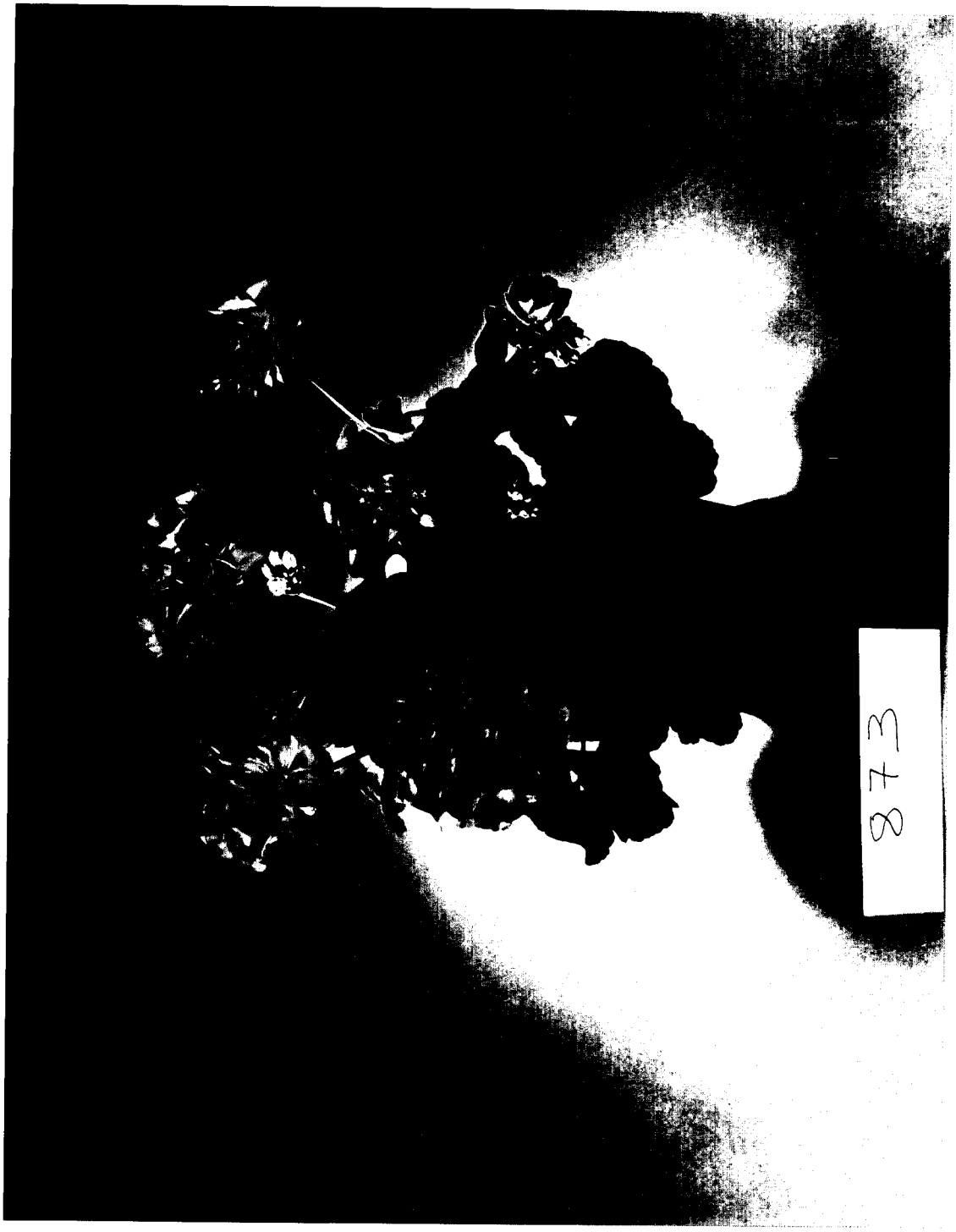
873